United States Patent [19]

Odenwälder et al.

[11] 4,310,621
[45] Jan. 12, 1982

[54] PHOTOSENSITIVE PHOTOGRAPHIC MATERIAL, A PROCESS FOR THE PRODUCTION OF PHOTOGRAPHIC IMAGES, DEVELOPMENT BATHS AND NEW HYDROQUINONES

[75] Inventors: Heinrich Odenwälder, Cologne; Karl Frank; Reinhard Müller, both of Leverkusen, all of Fed. Rep. of Germany

[73] Assignee: AGFA-Gevaert Aktiengesellschaft, Leverkusen, Fed. Rep. of Germany

[21] Appl. No.: 217,193

[22] Filed: Dec. 16, 1980

[30] Foreign Application Priority Data

Dec. 24, 1979 [DE] Fed. Rep. of Germany ....... 2952280

[51] Int. Cl.³ .......................... G03C 5/30; G03C 1/06
[52] U.S. Cl. .................... 430/443; 430/445; 430/448; 430/485; 430/505; 430/544; 430/566; 430/957; 430/959
[58] Field of Search ............... 430/443, 445, 505, 448, 430/957, 485, 382, 566, 544, 959

[56] References Cited

U.S. PATENT DOCUMENTS 3,961,963 6/1976 Shiba et al. .................. 430/957
4,105,452 8/1978 Shiba et al. .................. 430/959
4,187,110 2/1980 Yagihara et al. ............. 430/957

FOREIGN PATENT DOCUMENTS 2515213 10/1975 Fed. Rep. of Germany ...... 430/505

Primary Examiner—Mary F. Downey
Attorney, Agent, or Firm—Connolly and Hutz

[57] ABSTRACT

New DIR-compounds of the formula

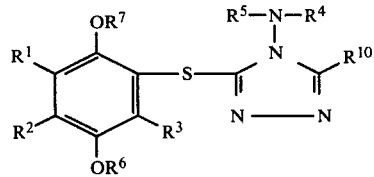

are useful in photographic materials and processes.

9 Claims, No Drawings

PHOTOSENSITIVE PHOTOGRAPHIC MATERIAL, A PROCESS FOR THE PRODUCTION OF PHOTOGRAPHIC IMAGES, DEVELOPMENT BATHS AND NEW HYDROQUINONES

This invention relates to a photographic material containing compounds capable of releasing development-inhibiting substances, to a process for the production of photographic images, to development baths and to new hydroquinones.

It is known that photographic materials may have incorporated in them compounds which release development inhibitors on reaction with colour developer oxidation products. Compounds such as these are, for example, the so-called DIR-couplers (DIR=Development Inhibitor Releasing) which are determined in U.S. Pat. No. 3,227,554. The compounds in question are colour couplers which, in the coupling position, contain a thioether substituent which, during colour coupling, in split off as a diffusing mercapto compound which has development-inhibiting properties and which is therefore capable of influencing the further development of the silver halide.

The use of DIR-couplers such as these improves the properties of the colour photographic materials in many respects. Thus, it is possible to control graininess, definition (sharpness) and gradation and, in this way, considerably to improve overall colour reproduction. In this connection, reference is made to the article entitled "Development-Inhibitor-Releasing (DIR) Couplers in Colour Photography" in Photographic Science and Engineering 13, 74 (1969).

Together with the development inhibitor released, the above-mentioned DIR couplers automatically form a dye. Accordingly, the particular DIR-coupler used has to be selected carefully if the balance of a colour photographic material in regard to colour is to be guaranteed. In particular, it is not possible to use the same DIR-coupler in all of the dye-forming and non-dye-forming layers of a colour photographic multilayer material because from the colour point of view, the dye formed generally coincides with the image dye in only one layer and, in the other two layers, would lead to an increase in the undesirable secondary density of the component colour image formed there.

These disadvantages do not arise if the DIR-couplers are replaced by compounds which are capable under the photographic development conditions of releasing development inhibitors without at the same time forming or releasing a dye. Compounds such as these are known as DIR-compounds to distinguish them from DIR couplers. One particularly important group of DIR-compounds is formed by the so-called DIR-hydroquinones which are known, for example, from U.S. Pat. Nos. 3,620,746 and 3,379,529 and from German Offenlegungsschrift No. 2,417,914.

The potential uses for DIR-hydroquinones are manifold, especially since they are also effective in cases where black-and-white developers, for example hydroquinones, are used. DIR-couplers are only effective where colour developer substances, for example of the p-phenylene diamine type, are used. The use of DIR-hydroquinones in chromogenic development is known from German Offenlegungsschrift No. 2,417,914 and from U.S. Pat. No. 3,364,022. Black-and-white development in the presence of DIR-hydroquinones is known for example from U.S. Pat. No. 3,639,417. This black-and-white development is generally the first development in known colour reversal processes. The use of DIR-hydroquinones in the initial development in colour reversal processes can lead to certain adverse effects. According to German Offenlegungsschrift No. 2,548,880 and British Pat. No. 1,515,167, adverse effects of DIr-hydroquinones are said to be able to be eliminated by carrying out the first development (equivalent to black-and-white development) in colour reversal processes for colour photographic silver halide reversal materials in the presence of a non-coupler compound, for example a DIR-hydroquinone, and subsequently contacting the photographic materials with an aqueous solution of a fogging agent.

The disadvantage of known DIR-compounds and their use is that, despite some improvement in the properties of photographic materials, other properties are still adversely affected. Thus, despite an improvement in definition or graininess, there is frequently a loss of sensitivity which has to be compensated by other measures, such as for example by increasing the silver coating (cf. U.S. Pat. No. 3,369,417). Particularly serious disadvantages are involved in the use of DIR-hydroquinones in reversal development processes and particularly in the use of DIR-hydroquinones in black-and-white development before colour development. In this case, colour density and definition can be reduced, as described in German Offenlegungsschrift No. 2,548,880. In addition, the known DIR-hydroquinones interfere seriously with the development of the threshold during colour development in colour reversal processes which can possibly be attributed to the fact that the development-inhibiting substances released during the first development remain adsorbed on the silver halide and are still capable of exerting a development-inhibiting effect during colour development.

Accordingly, one of the objects of the present invention is to find new DIR-compounds which avoid the disadvantages of the known compounds.

A photographic material comprising of a support and at least one photosensitive silver halide emulsion layer and, optionally, further layers has now been found, containing in one layer a DIR-compound which corresponds to formula (I) below:

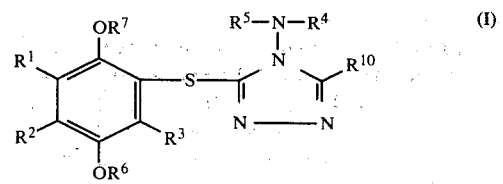

in which

R$^1$, R$^2$ and R$^3$ represent hydrogen, a hydrocarbon radical which may be substituted, a heterocyclic radical which may be substituted, an alkyl thio, alkyloxy or aryl thio radical which may be substituted, an amino group which may be substituted, OH or halogen; or R$^1$ and R$^2$ together represent the atoms required to complete a carbocyclic or heterocyclic ring;

R$^4$ and R$^5$ represent hydrogen, an alkyl radical which may be substituted, an acyl radical which may be substituted or R$^4$ and R$^5$ together represent the radical

$R^6$ and $R^7$ are hydrogen or a radical which can be split off in alkaline solution;

$R^8$ and $R^9$ represent hydrogen, an alkyl or aryl radical which may be substituted, a heterocyclic radical which may be substituted and $R^{10}$ represents hydrogen or an aryl or an alkyl radical.

A process for the production of photographic images has also been found, in which the development of an exposed photographic material is carried out at least partly in the presence of a compound corresponding to formula (I).

Photographic development baths have also been found which contain at least one photographic developer substance and a compound corresponding to formula (I).

Hydroquinones corresponding to formula (I) below have also been found

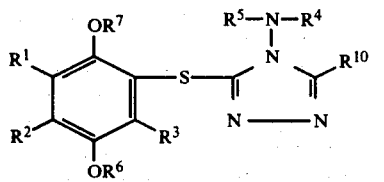

in which the substituents $R^1$ to $R^{10}$ are as defined above.

The alkyl radicals mentioned may contain in particular up to 20 carbon atoms. The aryl radicals mentioned are in particular phenyl or naphthyl radicals. The heterocyclic radicals mentioned preferably contain a 5-membered to 7-membered heterocyclic ring. Acyl radicals are understood in particular to the radicals which are derived from aliphatic or aromatic carboxylic acids and sulphonic acids, including carbonic acid monoesters, carbamic acids and sulphamic acids. Particularly preferred acyl radicals are acetyl, benzoyl, alkoxy carbonyl radicals, phenyloxy carbonyl radicals and N-phenyl carbamoyl radicals.

In a preferred embodiment, the substituents $R^1$ to $R^{10}$ in formula (I) have the following meanings: $R^1$, $R^2$ and $R^3$ represent hydrogen, an alkyl, alkenyl or aryl radical which may be substituted, a heterocyclic radical containing at least one 5-membered to 7-membered nitrogen-containing ring which may be substituted, an alkyl thio, alkyloxy or alkylamino radical which may be substituted, the alkyl portion containing from 1 to 20 carbon atoms;

phenyl thio, amino, acylamino, OH, chlorine, bromine, and/or $R^1$ and $R^2$ may together represent the atoms required to complete a heterocyclic or carbocyclic 5-membered or 6-membered ring, $R^4$ and $R^5$ represent hydrogen, an alkyl radical containing from 1 to 20 carbon atoms or an acyl radical derived from a carboxylic acid, or together, represent the group $=CR^8R^9$.

$R^6$ and $R^7$ represent hydrogen or an acyl radical which may be substituted $R^8$, $R^9$ represent hydrogen or an aryl radical, which may be substituted, and $R^{10}$ represents hydrogen.

In one particularly preferred embodiment, the substituents $R^1$ to $R^{10}$ in formula (I) have the following meanings:

$R^1$, $R^2$ and $R^3$ represent hydrogen, an alkyl radical containing from 1 to 4 carbon atoms which may be substituted or an alkyl thio radical containing from 10 to 20 carbon atoms, $R^4$ and $R^5$ represent hydrogen, benzoyl or, together, the radical

$R^6$ and $R^7$ represent hydrogen or an acetyl or benzoyl radical which may be substituted;

$R^8$ represents hydrogen, $R^9$ represents a phenyl or naphthyl radical substituted by at least one solubilising group, and $R^{10}$ represents hydrogen.

Solubilising groups are understood in particular to be hydroxyl, carboxyl and sulpho groups.

In addition, at least one of the substituents $R^1$ to $R^3$ may be a radical which imparts resistance to diffusion, particularly a long-chain alkyl radical. Radicals which impart resistance to diffusion are regarded as being radicals which make it possible for the compounds according to the invention to be incorporated in diffusion-resistant form in the hydrophilic colloids normally used in photographic materials. Preferred radicals of this type are organic radicals which, in general, may contain straight- or branched-chain aliphatic groups and possibly even carbocyclic or heterocyclic aromatic groups. The aliphatic moiety of these radicals generally contains from 8 to 20 carbon atoms. The radicals are attached to the remaining part of the molecule either directly or indirectly, for example through one of the following groups: —CONH—, —SO$_2$NH—, —CO—, —SO$_2$—, —NR— (where R is hydrogen or alkyl), —O— or —S—.

Particularly advantageous compounds correspond to formula (II) below:

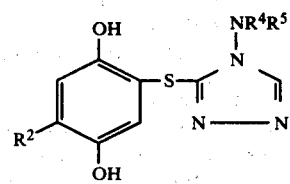

in which $R^2$ represents hydrogen, an alkyl radical, particularly containing from 1 to 20 carbon atoms which may be substituted, or an alkyl thio radical containing from 1 to 20 carbon atoms, $R^4$ and $R^5$ represent hydrogen, acyl or, together, form a methylidene group which may be substituted preferably containing an aryl or naphthyl group with a solubilising radical.

Particularly advantageous compounds corresponding to formula (II) are shown in Table 1 below:

TABLE 1

| Compound No. | R² | R⁴ | R⁵ | M.p.(°C.) |
|---|---|---|---|---|
| (1) | —S—C₁₂H₂₅ | >CH—⟨phenyl⟩—OH | | 160 |
| (2) | H | >CH—⟨phenyl⟩ with OH | | 243–244 |
| (3) | H | >CH—⟨naphthyl⟩ with HO | | 203 (Z.) |
| (4) | —S—C₁₂H₂₅ | >CH—⟨phenyl with COOH, OH, CH₃⟩ | | 176–177 |
| (5) | H | >CH—⟨phenyl⟩—OH | | 259–260(Z.) |
| (6) | H | H | —CO—O—⟨phenyl-COOH⟩ | 156–157(Z.) |
| (7) | H | >CH—⟨phenyl with COOH, OH, CH₃⟩ | | 235(Z.) |

Other advantageous compounds corresponding to the formula II are shown in Table 1a below:

TABLE 1a

| Compound No. | R² | R⁴ | R⁵ |
|---|---|---|---|
| (8) | H | >CH—⟨phenyl with OH⟩—NHSO₂—⟨phenyl⟩ | |
| (9) | H | >CH—⟨phenyl with OH, OCH₃⟩ | |
| (10) | H | >CH—⟨phenyl with OH⟩ | |
| (11) | H | >CH—⟨phenyl⟩—SO₃H | |
| (12) | H | >CH—⟨phenyl with OH, OH⟩ | |
| (13) | H | >CH—⟨furyl⟩ | |
| (14) | H | H | —CO—⟨phenyl⟩ |
| (15) | CH₃ | >CH—⟨phenyl with COOH, OH, CH₃⟩ | |

The compounds according to the invention are produced in known manner by the addition of a heterocyclic thione to a p-benzoquinone.

The production of compound 5 is described by way of example in the following. Production of compound 5

1st Stage 5.8 g of 4-amino-5-mercapto-1,2,4-triazole and 6.1 g of 4-hydroxy benzaldehyde are dissolved with stirring at 30° C. in 100 ml of methanol to which 5 ml of glacial acetic acid have been added. After stirring for one hour at room temperature, a deposit appears. Precipitation of the deposit is completed with cooling. After filtration under suction and washing with a little ice-cold methanol, 8.5 g of 4-(4-hydroxybenzylideneamino)-5-mercapto-1,2,4-triazole melting at 247° to 248° C. are obtained.

C calculated—49.2%; observed—48.9%. H calculated—3.6%; observed—3.6%. N calculated—25.5%; observed—25.3%.

2nd Stage 13.2 g of the compound obtained in the first stage are dissolved in 600 ml of methanol to which 15 ml of 5 N HCl have been added. 6.48 g of p-benzoquinone are introduced in portions with stirring at room temperature, after which the reaction mixture is stirred for 4 hours at room temperature and then poured into 1.5 liters of water. The deposit is filtered off under suction, washed with water and then stirred with 200 ml of isopropanol. Filtration under suction and drying in air gives 15.6 g of compound No. 5 which melts with decomposition at 259° to 260° C.

C calculated—54.8; observed—54.1. H calculated—3.7; observed—3.6. N calculated—17.1; observed—17.1.

The photographic material according to the invention is, in particular, a colour photographic multilayer material which, in at least one of its layers, contains a compound corresponding to formula (I) which may be incorporated into a photosensitive silver halide emulsion layer or into a hydrophilic binder layer which is associated with a photosensitive silver halide emulsion layer, but which does not itself have to be photosensitive. In the present context, the term "associated" applies to a layer which is situated in such a spatial relationship with the photosensitive silver halide emulsion layer that, during development of the silver halide emulsion layer, significant quantities of oxidised developer appear therein through diffusion from the photosensitive silver halide emulsion layer.

The concentration of the compound of formula (I) according to the invention in the particular layer may be varied within wide limits, for example between $1 \times 10^{-3}$ and $300 \times 10^{-3}$ moles per kg of silver halide and, in associated binder layers, between limits of for example $0.5 \times 10^{-3}$ to $1 \times 10^{-3}$ moles per gram of binder. In general, the DIR-compound is present in the material in a quantity of from $10^{-4}$ to $10^{-1}$ moles per mole of silver halide. The concentration depends upon the particular application intended, upon the silver halide emulsion used and upon whether the compound is situated in a silver halide emulsion layer or in a non-photosensitive binder layer. The upper limit is generally at concentrations in which color couplers are also used in photographic layers. However, it is not essential to keep to this limit.

The inhibiting effect of the compounds according to the invention may be developed both in the layer containing the compounds according to the invention where it contains developable silver halide and also in adjacent silver halide emulsion layers into which the inhibitor released during development from the compound of formula (I) is capable of diffusing. In this way, it is possible by means of the compounds according to the invention to control development separately in each of the individual photosensitive silver halide emulsion layers. Using the interlayer effects made possible by means of the compounds according to the invention, the development of a silver halide emulsion layer may also be influenced by the outcome of imagewise development in another layer so that it is possible to obtain an overall improvement in regard to graininess, definition and colour reproduction.

In order to obtain special effects, the compounds according to the invention may be combined with one another or even with other known DIR-compounds or DIR-couplers. Particular reference is made in this connection to German Offenlegungsschrift No. 2,509,722.

In one preferred embodiment, the photosensitive silver halide emulsion layers of th photographic material according to the invention have different spectral sensitivities and at least one non-diffusing compound is associated with each of them to produce an image dye having a colour which is generally complementary to the spectral sensitivity. The compounds in question may be the usual colour couplers which are in general, incorporated in the silver halide emulsion layers themselves. Thus, in one preferred embodiment, the red-sensitive layer contains for example a non-diffusing colour coupler for producing the cyan component dye image, generally a coupler based on phenol or α-naphthol, the green-sensitive layer contains at least one non-diffusing colour coupler for producing the magenta component dye image, normally a colour coupler based on 5-pyrazolone or indazolone, and finally the blue-sensitive layer contains at least one non-diffusing colour coupler for producing the yellow component dye image, generally a colour coupler containing an open-chain keto-methylene group. Large numbers of colour couplers of these types are known and are described in numerous Patent specifications. For example, reference is made here to the article entitled "Farbkuppler (colour Couplers)" by W. Pelz in "Mitteilungen aus den Forschungslaboratorien der Agfa, Leverkusen/Munchen", Vol. III (1961). The non-diffusing colour couplers may contain a removable substitutent in the coupling position, so that, for dye formation, they require only two equivalents of silver halide in contrast to the usual 4-eqivalent couplers. In general, the colour couplers used are themselves colourless. However, if the removable substituent contains a chromophoric group, as is the case with the known masking couplers, the colour couplers generally have a colour which is, suitable for masking undesirable secondary densities of the image dye by standard masking techniques. The image dyes produced from colour couplers are generally resistant to diffusion.

If one or more silver halide emulsion layers of the material according to the invention is/are in the form of a double layer consisting of two component layers which may have different sensitivity or a different silver-to-coupler ratio, as has been proposed on various occasions with the object of obtaining a better sensitivity-graininess reaction, i.e. with the object of increasing sensitivity whilst, at the same time, avoiding any coarsening of the dye grain (cf. for example German Pat. No. 1,121,470; U.S. Pat. No. 3,726,681; German Offenlegungsschrifts Nos. 2,322,165 and 2,416,982), one or even each of these component layers of a double layer according to the invention may contain one or more of the DIR-compounds according to the invention.

However, the image dyes may also be produced initially in diffusing form during development and only fixed after transfer to an image-receiving layer, as is known from various dye diffusion transfer processes, for example from U.S. Pat. Nos. 3,227,550 and 3,628,952 and from German Pat. No. 1,772,929. In this case, colourless or coloured non-diffusing dye-producing compounds are associated with the photosensitive silver halide emulsions, releasing diffusing dyes to form an image during the development process. Dye-producing compounds such as these are incorporated either in the silver halide emulsion layer or in an associated hydrophilic binder layer which may contain for example development nuclei and, may also contain silver halide which may even be developed without exposure.

In cases where standard silver halide emulsions are used in combination with non-diffusing colour couplers or with non-diffusing dye-producing compounds, negative dye images are normally obtained. However, the compounds according to the invention may be used with advantage in reversal processes, in which case positive images are obtained. The reversal processes in question are standard reversal processes in which the photographic material is first subjected after image-wise exposure to an initial development (black-and-white development) and is then colour-developed after or during a reversal fogging treatment, for example by diffuse second exposure or by chemical fogging, and also reversal processes in which a reversal of the image information takes place in the photographic material due to the presence of the DIR-compounds according to the invention. This may occur for example when a spontaneously developable (i.e. without exposure) silver halide emulsion layer containing a colour coupler or a dye-producing compound is arranged adjacent to a standard silver halide emulsion layer containing a DIR-compound. It is clear that a procedure such as this requires DIR-couplers or DIR-compounds which release the inhibitor as quickly as possible so that it inhibits development imagewise in the spontaneously developable layer.

The non-diffusing, development-inhibitor-releasing compounds used in accordance with the invention are added to the photosensitive silver halide emulsions or other casting solutions by methods known per se. Where the compounds in question are soluble in water or alkalis, they may be added to the emulsions in the form of aqueous solutions, to which water-miscible organic solvents, such as ethanol, acetone or dimethyl formamide may be added. Where the non-diffusing colour couplers, dye-producing compounds and development-inhibitor-releasing compounds are water-insoluble or alkali-insoluble compounds, they may be emulsified in known manner, for example by mixing a solution of these compounds in a low-boiling organic solvent either directly with the silver halide emulsion or first with an aqueous gelatin solution, followed by evaporation of the organic solvent. A gelatin emulsion of the particular comound obtained in in this way is then mixed with the silver halide emulsion. So-called coupler solvents or oil formers may additionally be used for incorporating hydrophobic compounds such as these by emulsification. Coupler solvents or oil formers are generally relatively high boiling organic compounds which include the non-diffusing colour couplers and development-inhibitor-releasing compounds to be emulsified in the silver halide emulsions in the form of oily droplets. In this connection, reference is made for example to U.S. Pat. Nos. 2,322,027; 3,689,271; 3,764,336 and 3,765,897. Where the compounds according to the invention are emulsified in the layers using oil formers of the type in question, the presence of radicals imparting resistance to diffusion in the compounds according to the invention does not have to meet such stringent requirements because, in this case, even shorter alkyl radicals, for example isoamyl radicals, are occasionally sufficient for preventing diffusion of the compounds according to the invention in the layers of the photographic material.

It is also possible to prepare aqueous dispersions of the DIR-compounds according to the invention and to add them to the particular casting solutions. To this end, aqueous suspensions of the compounds are finely ground, for example by intensive stirring in the presence of sharp-edged sand and/or by applying ultrasound, optionally in the presence of a suitable hydrophilic binder, such as gelatin.

The usual silver halide emulsions are suitable for the purposes of the invention. They may contain as silver halide silver chloride, silver bromide or mixtures thereof, which may have a small silver iodide content of up to 10 mole percent. The emulsions may be standard negative emulsions and also direct-positive emulsions, for example of the type characterised by high sensitivity within the silver halide grains, for example emulsions of the type described in U.S. Pat. No. 2,592,250.

Gelatin is preferably used as binder for the photographic layers. However, it may also be completely or partly replaced by other natural or synthetic binders.

The emulsions may also be chemically sensitised, for example by the addition during chemical ripening of sulphur-containing compounds, for example allyl isothiocyanate, allyl thiourea and sodium thiosulphate. Other suitable chemical sensitisers are reducing agents, for example the tin compounds described in Belgian Pat. Nos. 493,464 or 568,687, also polyamines such as diethylene triamine or aminoethyl sulphinic acid derivatives, for example according to Belgian Pat. No. 547,323. Other suitable chemical sensitisers are noble metals and noble metal compounds, such as gold, platinum, palladium, iridium, ruthenium or rhodium. It is also possible to sensitise the emulsions with polyalkylene oxide derivatives, for example with polyethylene oxide having a molecular weight in the range from 1000 to 20,000, with condensation products of alkylene oxides and alcohols, aliphatic carboxylic acids, aliphatic amines, aliphatic diamines and amides.

The emulsions may even be optically sensitised, for example with the usual polymethine dyes, such as neutrocyanines, basic or acid carbocyanines, rhodacyanines, hemicyanines, styryl dyes, oxonols and the like. Sensitisers such as these are described in F. M. Hamer's book entitled "The Cyanine Dyes and Related Compounds" (1964).

The emulsions may contain the usual stabilisers such as, for example, homopolar or salt-like compounds of mercury with aromatic or heterocyclic rings, such as mercapto triazoles, single mercury salts, sulphonium-mercury double salts and other mercury compounds. Other suitable stabilisers are azaindenes, preferably tetra- or penta-azaindenes, particularly those substituted by hydroxyl or amino groups. Compounds of this type are described, for example, in the article by Birr in Z. Wiss. Phot. 47 (1952), pages 2 to 58. Other suitable stabilisers are inter alia heterocyclic mercapto compounds, for example phenyl mercaptotetrazole, quaternary benzthiazole derivatives and benzotriazole.

The layers of the photographic material may be hardened in the usual way, for example with formaldehyde or halogen substituted aldehydes containing a carboxyl group, such as mucobromic acid, diketones, methane sulphonic acid esters, dialdehydes and the like. The photographic layers may also be hardened with epoxide, the heterocyclic ethylene imine or acryloyl hardeners. It is also possible to harden the layers by the process according to German Offenlegungsschrift No. 2,218,009 in order to obtain colour photographic materials which are suitable for processing at high temperatures. The photographic layers or the colour photographic multilayer materials may also be hardened with diazine, triazine or 1,2-dihydroquinoline hardeners. Examples of hardeners such as these are diazine derivatives containing alkyl or aryl sulphonyl groups, derivatives of hydrogenated diazines or triazines such as, for example, 1,3,5-hexahydrotriazine, fluorine-substituted diazine derivatives such as, for example, fluoropyrimidine, esters of disubstituted 1,2-dihydroquinoline or 1,2-dihydroisoquinoline-N-carboxylic acids. Other suitable hardeners are vinyl sulphonic acid hardeners, carbodiimide or carbamoyl hardeners of the type described, for example, in German Offenlegungsschrifts Nos. 2,263,602; 2,225,230 and 1,808,685; French Pat. No. 1,491,807, German Pat. No. 872,153 and East German Pat. No. 7218. Other suitable hardeners are described, for example, in British Pat. No. 1,268,550.

The compounds according to the invention may also be contained in a black-and-white or colour developer. They may be contained in particular in the first developer (black-and-white developer) in colour reversal processing. In reversal processes of this type, the colour photographic material, having been exposed to form an image, is subjected to a first development (black-and-white development) to develop the exposed silver halide. The residual silver halide is then diffusely exposed or chemically fogged and then treated with a colour developer. This is followed by standard bleaching and fixing which may even be combined. The standard auxiliary baths may be used before and between the above-mentioned stages.

Suitable black-and-white developer baths generally have a pH-value above 8 and may contain the usual black-and-white developer compounds such as, for example, dihydroxy benzenes (for example hydroquinone), pyrazolidones (for example 1-phenyl-3-pyrazolidone), aminophenols, 1-phenyl-3-pyrazolines etc. The usual colour developer baths which, in general, also have a pH-value above 8 may be used for colour development. It is possible to use the usual colour developer substances, for example N,N-dimethyl-p-phenylene diamine, 4-amino-3-methyl-N-ethyl-N-methoxy ethylene aniline, 2-amino-5-diethylaminotoluene, N-butyl-N-ωsulphobutyl-p-phenylene diamine, 2-amino-5-(N-ethyl-N-β-methanesulphonamidoethylamino)-toluene, N-ethyl-N-β-hydroxy-ethyl-p-phenylene diamine, N,N-bis-(β-hydroxyethyl)-p-phenylene diamine, 2-amino-5-(N-ethyl-N-β-hydroxyethylamino)-toluene. Other suitable colour developers are described for example in J. Amer. Chem. Soc. 73, 3100 (1951).

The developer baths used may contain the usual additives, such as preservatives, alkaline agents, buffer substances, anti-fogging agents and antilime agents. Chemical fogging may be carried out with the usual substances, for example with boron hydrides, amines and, in particular, tin compounds. The treatment in the various baths may be carried out at the usual temperatures, optionally at temperatures higher than 30° C.

The concentration of the compounds according to the invention in photographic developers is generally between 1 mg and 1000 mg per liter and particularly between 5 mg and 100 mg per liter of the developer.

The invention is illustrated by but in no way limited to the following Examples.

EXAMPLE 1

A standard colour photographic reversal multilayer material is produced by applying the following layers to a support layer:

(a) a red-sensitive silver halide emulsion containing a cyan coupler corresponding to the following formula

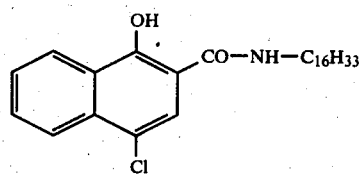

(b) a green-sensitive silver halide emulsion containing a magenta coupler corresponding to the following formula

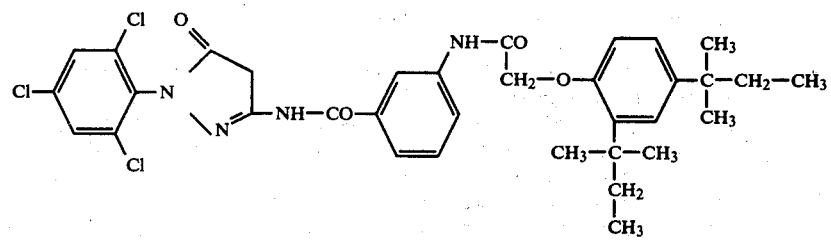

(c) a blue-sensitive silver halide emulsion containing a yellow coupler corresponding to the following formula

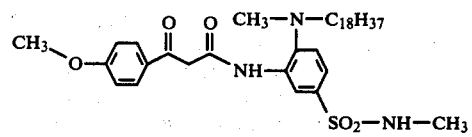

The material is hardened with a standard hardener. After exposure, the material is subjected to the following reversal process steps at 40° C. using the baths indicated:

Variant 1, comparison

| Process steps | Time(s) |
|---|---|
| First development | 120 |
| Stop bath 1 | 20 |
| Rinsing | 40 |
| 2nd Exposure | |
| Colour development | 180 |
| Stop bath 2 | 60 |
| Rinsing | 60 |
| Bleaching | 60 |
| Rinsing | 40 |
| Fixing | 40 |
| Rinsing | 120 |

The black-and-white developer baths used for the first development have the following composition:

| | |
|---|---|
| Ethylene diamine tetraacetic acid | 2 g/l |
| Sodium carbonate | 20 g/l |
| Sodium sulphite | 50 g/l |
| 1-phenyl-3-pyrazolidone | 0.3 g/l |
| Hydroquinone | 6.0 g/l |
| Potassium thiocyanate | 1.25 g/l |
| Potassium bromide | 2.0 g/l |
| Potassium iodide | 40 mg/l |
| Sodium bisulphite | 3.0 g/l |

The colour developer used for colour development had the following composition:

| | |
|---|---|
| Ethylene diamine tetraacetic acid | 2 g/l |
| Trisodium phosphate | 20 g/l |
| Sodium sulphite | 2 g/l |
| Hydroxyl amine sulphate | 1 g/l |
| 4-amino-3-methyl-N-ethyl-N-(-62 - hydroxyethyl)-aniline | 4.2 g/l |
| Potassium bromide | 0.8 g/l |
| Citrazinic acid | 1.5 g/l |
| Potassium iodide | 30 mg/l |

Variant 2, invention:
Processing is carried out in the same way as in variant 1, except that the first developer additionally contains 200 mg/l of compound number 5.

Variant 3, invention:
Processing is carried out in the same way as in variant 1, except that the first developer additionally contains 100 mg of compound number 7.

The modulation transfer function (MTF) is used as the test criterion. It is desired for example in the US Standard ANSI PH 2.39-1977 and in the Journal "Fotografische Korrespondenz" 1963, pages 35 to 45 and 69 to 80. The transfer factors for the lines/mm indicated are shown in Table 2 below.

TABLE 2

| | Transfer Factor for | | | | | |
|---|---|---|---|---|---|---|
| | 1 | 5 | 10 | 20 | 30 | 40 lines/mm |
| Yellow layer | | | | | | |
| variant 1, standard | 100 | 100 | 95 | 80 | 71 | 59 |
| variant 2 | 100 | 100 | 98 | 86 | 75 | 62 |
| variant 3 | 100 | 105 | 100 | 86 | 73 | 60 |
| Magenta layer | | | | | | |
| variant 1, standard | 100 | 100 | 98 | 88 | 72 | 60 |
| variant 2 | 100 | 105 | 107 | 97 | 80 | 64 |
| variant 3 | 100 | 111 | 114 | 102 | 83 | 65 |
| Cyan layer | | | | | | |
| variant 1, standard | 100 | 100 | 92 | 73 | 52 | 35 |
| variant 2 | 100 | 104 | 105 | 84 | 56 | 35 |
| variant 3 | 100 | 104 | 109 | 87 | 64 | 39 |

It follows from Table 2 that, in the range from 5 to 40 lines/mm, a distinct improvement in definition is obtained with the compounds according to the invention.

EXAMPLE 2

A standard colour photographic reversal multilayer material is produced by applying the following layers to a support layer:

(a) a red-sensitive silver halide emulsion containing a cyan coupler corresponding to the following formula

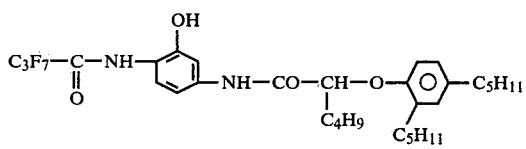

(b) a green-sensitive silver halide emulsion containing a magenta coupler corresponding the following formula

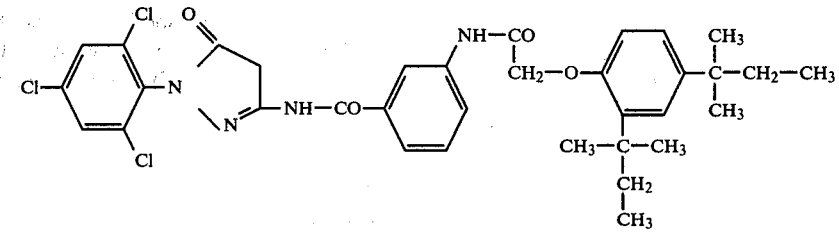

(c) a blue-sensitive silver halide emulsion containing a yellow coupler corresponding to the following formula

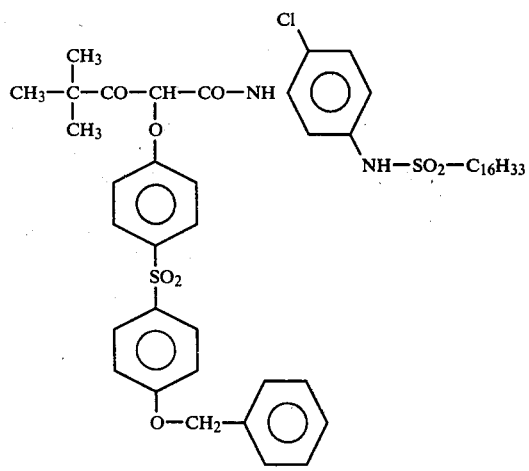

The material is hardened with a standard hardener. After exposure, the material is subjected to the following reversal process steps at 38° C. using the baths indicated:

| Process step | Time (minutes) |
|---|---|
| First development | 6 |
| Rinsing | 2 |
| Fogging bath | 2 |
| Colour development | 6 |

The material is then bleached, fixed and rinsed in the usual way.

The developer baths used had the following compositions:

| Sample 1: First developer: | |
|---|---|
| Nitrilotrimethylene triphosphonic acid | 1 ml |
| Potassium sulphite (45% solution) | 44 ml |
| Sodium bromide | 2.2 g |
| Sodium thiocyanate | 1 g |
| Potassium iodide | 4.5 mg |
| Potassium hydroxide (45% solution) | 7 ml |
| Diethylene glycol | 12.0 ml |
| Hydroxymethyl-methylphenidone | 1.4 g |
| Potassium carbonate | 14.0 g |
| Sodium bicarbonate | 12.0 g |
| potassium hydroquinone monosulphonate | 22.0 g |
| Water to 1 liter | |

| Colour developer: | |
|---|---|
| Nitrilotrimethylene triphosphonic acid | 5.0 ml |
| Phosphoric acid (85%) | 6.9 ml |
| Sodium bromide | 0.65 g |
| Potassium iodide | 30.0 mg |
| Potassium hydroxide (45% solution) | 31.0 ml |
| Sodium sulphite | 4.5 g |
| Citrazinic acid | 1.25 g |
| 4-amino-N-ethyl-N-(β-ethane-sulphonamido-ethyl)-m-toluidine-sesquisulphate (monohydrate) | 11.0 g |
| 2,2-ethylene dithiodiethanol | 1.0 g |
| Water to 1 liter | |

Sample 2 (Comparison)

The treatment was carried out in the same way as for Sample 1 except that 100 mg of the compound 2,5-dimethyl-3-(1-phenyl-5-tetrazolylthio)-hydroquinone known from German Offenlegungsschrift No. 2,548,880 were added to the first developer.

Sample 3 (invention)

The treatment was carried out in the same way as for Sample 1, except that 100 mg of compound number 7 according to the invention were added to the first developer.

The results obtained after evaluation in accordance with Example 1 are shown in Table 3 below. In contrast to Example 1, however, measurement was only carried out behind a filter whose spectral permeability corresponds to the spectral sensitivity distribution of human eyesight (known as Vλ-distribution according to DIN 5033). Accordingly, the measurement corresponds to the visual impression of sharpness.

TABLE 3

| | Transfer factors for | | | | | |
|---|---|---|---|---|---|---|
| | 1 | 5 | 10 | 20 | 30 | 40 L/mm |
| Sample 1, standard | 100 | 100 | 99 | 82 | 65 | 47 |
| Sample 2, comparison | 100 | 102 | 100 | 86 | 70 | 52 |
| Sample 3, invention | 100 | 104 | 104 | 92 | 76 | 56 |

It follows from Table 3 that the compounds according to the invention are superior to the compounds known from German Offenlegungsschrift No. 2,548,880.

We claim:

1. A photographic material comprising a support and at least one photosensitive silver halide emulsion layer and further layers which contains a DIR-compound in one layer, wherein the DIR-compound corresponds to formula (I) below

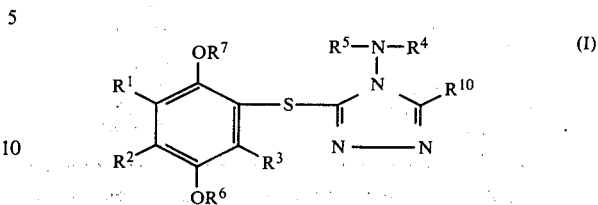

in which

R$^1$, R$^2$ and R$^3$ represent hydrogen, a hydrocarbon radical which may be substituted, a heterocyclic radical which may be substituted, an alkylthio, alkyloxy or arylthio radical which may be substituted, an amino group which may be substituted, OH or halogen, or R$^1$ and R$^2$ together represent the atoms required to complete a carbocyclic or heterocyclic ring, R$^4$ and R$^5$ represent hydrogen, an alkyl radical which may be substituted or an acyl radical which may be substituted or, may together, form the radical

R$^6$ and R$^7$ represent hydrogen or a radical capable of being split off in alkaline solution, R$^8$ and R$^9$ represent hydrogen, an alkyl or aryl radical which may be substituted or a heterocyclic radical which may be substituted, and R$^{10}$ represents hydrogen, an aryl radical or an alkyl radical.

2. A material as claimed in claim 1, wherein R$^1$, R$^2$ and R$^3$ represent hydrogen, an alkyl, alkenyl or aryl radical which may be substituted, a heterocyclic radical containing at least one 5-membered to 7-membered nitrogen-containing ring which may be substituted, an alkylthio, alkyloxy or alkylamino radical which may be substituted, the alkyl portion containing from 1 to 20 carbon atoms, phenylthio, amino, OH, chlorine, bromine, acylamino and/or R$^1$ and R$^2$ together represent the radical required to complete a heterocyclic or carbocyclic 5-membered to 6-membered ring, R$^4$ and R$^5$ represent hydrogen, an alkyl radical containing from 1 to 20 carbon atoms or an acyl radical derived from a carboxylic acid or, together, form the radical =C R$^8$ R$^9$, R$^6$ and R$^7$ represent hydrogen, an acyl radical, which may be substituted, R$^8$ and R$^9$ represent hydrogen or an aryl radical, which may be substituted, and R$^{10}$ represents hydrogen.

3. A process for the production of photographic images by developing an exposed silver halide photographic material, wherein at least one stage of the development process is carried out in the presence of a compound corresponding to formula (I) below:

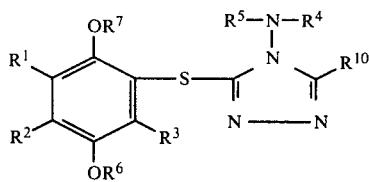 (I)

in which
- $R^1$, $R^2$ and $R^3$ represent hydrogen, a hydrocarbon radical which may be substituted, a heterocyclic radical which may be substituted, an alkylthio, alkoxy or arylthio radical which may be substituted, an amino group, OH or halogen, or $R^1$ and $R^2$ together represent the radical required to complete a carbocyclic or heterocyclic ring,
- $R^4$ and $R^5$ represent hydrogen, an alkyl radical which may be substituted, an acyl radical which may be substituted or, together, form the radical

- $R^6$ and $R^7$ represent hydrogen or a radical capable of being split off in alkaline solution,
- $R^8$ and $R^9$ represent hydrogen, an alkyl or aryl radical which may be substituted or a heterocyclic radical which may be substituted and
- $R^{10}$ represents hydrogen or an aryl or an alkyl radical.

4. A process as claimed in claim 3, wherein
- $R^1$, $R^2$ and $R^3$ represent hydrogen, an alkyl, alkenyl or aryl radical which may be substituted, a heterocyclic radical containing at least one 5-membered to 7-membered nitrogen-containing ring which may be substituted, an alkylthio, alkyloxy or alkylamino radical, the alkyl portion containing from 1 to 20 carbon atoms, which may be substituted, phenyl thio, amino, OH, chlorine, bromine, an acylamino radical, and/or $R^1$ and $R^2$ together form the radical required to complete a heterocyclic or carbocyclic 5-membered to 6-membered ring,
- $R^4$ and $R^5$ represent hydrogen, an alkyl radical containing from 1 to 20 carbon atoms or an acyl radical derived from a carboxylic acid, or together, form the radical $=C\ R^8\ R^9$,
- $R^6$ and $R^7$ represent hydrogen or an acyl radical which may be substituted.
- $R^8$ and $R^9$ represent hydrogen or an aryl radical which may be substituted,
- $R^{10}$ represents hydrogen.

5. A process as claimed in claim 3, wherein
- $R^1$, $R^2$ and $R^3$ represent hydrogen, an alkyl radical containing from 1 to 4 carbon atoms which may be substituted or an alkylthio radical containing from 10 to 20 carbon atoms,
- $R^4$ and $R^5$ represent hydrogen, benzoyl or, together, form the radical

- $R^6$ and $R^7$ represent hydrogen or an acetyl or benzoyl radical which may be substituted,
- $R^8$ represents hydrogen,
- $R^9$ represents a phenyl or naphthyl radical substituted by at least one solubilising group, and
- $R^{10}$ represents hydrogen.

6. A process as claimed in claim 3, wherein the DIR-compound corresponds to the following formula

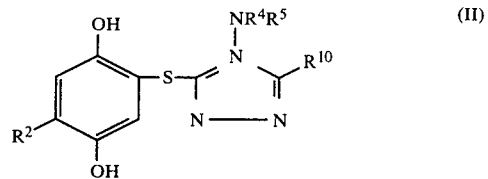 (II)

in which
- $R^2$ represents hydrogen, an alkyl radical, particularly containing from 1 to 20 carbon atoms which may be substituted, or an alkylthio radical containing from 1 to 20 carbon atoms,
- $R^4$ and $R^5$ represents hydrogen, acyl or, together, form a methylidene group which may be substituted preferably containing an aryl or naphthyl group with a solubilising radical.

7. A process as claimed in claim 3, wherein the development process is a colour reversal development process including a first development step and a following colour development step.

8. A process as claimed in claim 7, wherein the compound corresponding to formula (I) is contained in the first developer in a quantity of from 1 mg to 1000 mg.

9. A photographic developer bath for photosensitive silver-halide-containing materials containing at least one developer substance and a DIR-compound, wherein the DIR-compound corresponds to formula (I) below:

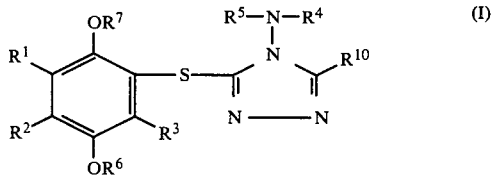 (I)

in which
- $R^1$, $R^2$ and $R^3$ represent hydrogen, a hydrocarbon radical which may be substituted, a heterocyclic radical which may be substituted, an alkylthio, alkyloxy or aryl thio radical which may be substituted, an amino group which may be substituted, OH or halogen, or $R^1$ or $R^2$ together represent the radical required to complete a carbocyclic or heterocyclic ring,
- $R^4$ and $R^5$ represent hydrogen, an alkyl radical which may be substituted, an acyl radical which may be substituted or, together, form the radical

- $R^6$ and $R^7$ represent hydrogen or a radical capable of being split off in alkaline solution,
- $R^8$ and $R^9$ represent hydrogen, an alkyl or aryl radical which may be substituted or a heterocyclic radical which may be substituted and
- $R^{10}$ represents hydrogen or an alkyl radical.

* * * * *